US00PP35275P3

(12) United States Plant Patent
Meilland

(10) Patent No.: US PP35,275 P3
(45) Date of Patent: Jul. 25, 2023

(54) BEDDING ROSE PLANT NAMED 'MEICOSME'

(50) Latin Name: *Rosa hybrida*
Varietal Denomination: MEICOSME

(71) Applicant: The Conard Pyle Company, West Grove, PA (US)

(72) Inventor: Alain Antoine Meilland, Antibes (FR)

(73) Assignee: The Conard Pyle Company, West Grove, PA (US)

( * ) Notice: Subject to any disclaimer, the term of this patent is extended or adjusted under 35 U.S.C. 154(b) by 45 days.

(21) Appl. No.: 17/888,777

(22) Filed: Aug. 16, 2022

(65) Prior Publication Data

US 2023/0069825 P1 Mar. 2, 2023

(30) Foreign Application Priority Data

Aug. 27, 2021 (QZ) ..... PBR 2021/2142

(51) Int. Cl.
*A01H 5/02* (2018.01)
*A01H 6/74* (2018.01)

(52) U.S. Cl.
USPC ..... Plt./107
CPC ..... *A01H 6/749* (2018.05)

(58) Field of Classification Search
USPC ..... Plt./107
CPC ..... A01H 5/749
See application file for complete search history.

(56) References Cited

U.S. PATENT DOCUMENTS

PP11,836 P2 4/2001 Radler
PP20,175 P2 7/2009 Meilland

OTHER PUBLICATIONS

Meilland Roses and Creation, Discover our 2 New ADR Varieties (https://meilland.com/en/discover-our-2-new-adr-varieties, downloaded on Sep. 8, 2022.*

* cited by examiner

*Primary Examiner* — Anne Marie Grunberg
(74) *Attorney, Agent, or Firm* — Panitch Schwarze Belisario & Nadel LLP; Stephany G. Small; Travis W. Bliss

(57) ABSTRACT

A new and distinct variety of rose plant, referred to by its cultivar name, 'MEICOSME', is disclosed. The new variety forms attractive, single dark pink purple colored flowers. Attractive semi-glossy foliage is formed, which contrasts beautifully with the blossoms. A bushy growth habit is displayed. The new variety is well suited for providing attractive ornamentation in the landscape.

1 Drawing Sheet

Latin name of genus and species of plant claimed: *Rosa hybrida.*

Variety denomination: 'MEICOSME'.

CROSS REFERENCE TO RELATED APPLCIATIONS

This application claims priority to Plant Breeders' Right Application Number 2021/2142, which was filed at Community Plant Variety Office in the European Union on Aug. 27, 2021, the contents of which are hereby incorporated by reference for all purposes.

STATEMENT REGARDING PRIOR DISCLOSURES BY THE INVENTOR

The first offer for sale of the new variety was Feb. 22, 2021 in France. The first offer for sale of the new variety was by the inventor or another who obtained the new variety directly or indirectly from the inventor. No plants of the new variety have been sold in this country or anywhere in the world, nor has any disclosure of the new plant been made, more than one year prior the effective filing date of this application, and such sale or disclosure within one year was either derived directly or indirectly from the inventor.

BACKGROUND OF THE INVENTION

The new variety of bedding rose plant of the present invention was created by controlled breeding at Le Cannet des Maures, Var, France by artificial pollination wherein two parents were crossed which previously had been studied in the hope that they would contribute the desired characteristics. The female parent (i.e., the seed parent) of the new variety was an unnamed seedling (not patented) from the cross between the 'MEINOIRAL' variety (not patented) and an unnamed seedling (not patented). The male parent (i.e., the pollen parent) of the new variety was the 'MEIZMEA' variety (U.S. Plant Pat. No. 20,175).

The parentage of the new variety can be summarized as follows:

('MEINOIRAL' x Unnamed Seedling) x 'MEIZMEA'

The seeds resulting from the above pollination were sown and small plants were obtained which were physically and biologically different from each other. Selective study resulted in the identification of a single plant of the new variety.

The new variety has been found to undergo asexual propagation in Le Cannet des Maures, Var, France by a number of routes, including eye budding, softwood cuttings, and hardwood cuttings. Asexual propagation by the above-mentioned techniques in Le Cannet des Maures, Var, France has shown that the characteristics of the new variety are stable and are strictly transmissible by asexual propagation from one generation to another. Accordingly, the new variety undergoes asexual propagation in a true-to-type manner.

SUMMARY OF THE INVENTION

It was found that the new variety of rose plant of the present invention possesses the following combination of characteristics:

(a) forms dark pink purple colored flowers, (b) produces single flowers, and (c) exhibits a bushy growth habit.

The new variety well meets the needs of the horticultural industry. It can be grown to advantage as ornamentation in parks, gardens, public areas, and in residential settings. Accordingly, the plant is particularly well suited for growing in the landscape.

The new variety of the present invention can readily be distinguished from its ancestors. More specifically, the unnamed seed parent ('MEINOIRAL' x Unnamed Seedling) produces medium pink colored flowers, whereas the new variety produces dark pink purple colored flowers. In addition, the 'MEIZMEA' variety (i.e., pollen parent) displays flowers with a light pink colored spot at the base of the flower, whereas the new variety displays a yellow-white colored spot at the base of the flower. Moreover, the new variety can be readily distinguished from other similar non-parental varieties. For example, the 'RADRAZZ' variety (U.S. Plant Pat. No. 11,836) produces red colored semi-double flowers, whereas the new variety produces dark pink purple colored single flowers.

The new variety has been named 'MEICOSME'.

BRIEF DESCRIPTION OF THE PHOTOGRAPH

The accompanying photograph of the drawing shows as nearly true as it is reasonably possible to make the same, in a color illustration of this character, typical specimens of the plant parts of the new variety. The rose plants of the new variety were approximately one year of age and were observed during September while budded on their own roots and growing outdoors at Le Cannet des Maures, Var, France. Dimensions in centimeters are indicated at the bottom of the drawing.

Element 1—illustrates a specimen of a young shoot.

Element 2—illustrates a specimen of a floral bud before the opening of the sepals.

Element 3—illustrates a specimen of a floral bud at the opening of the sepals.

Element 4—illustrates a specimen of a floral bud at the opening of the petals.

Element 5—illustrates a specimen of a flower in the course of opening.

Element 6—illustrates a specimen of an open flower — plan view — reverse.

Element 7—illustrates a specimen of an open flower — plan view — obverse.

Element 8—illustrates a specimen of a fully open flower — plan view — reverse.

Element 9—illustrates a specimen of a fully open flower — plan view — obverse.

Element 10—illustrates a specimen of a floral receptacle showing arrangement of the pistils (stamens removed).

Element 11—illustrates a specimen of a floral receptacle showing arrangement of the stamens and pistils.

Element 12—illustrates a specimen of a flowering stem.

Element 13—illustrates a specimen of a leaf with 3 leaflets — plan view — upper surface.

Element 14—illustrates a specimen of a leaf with 5 leaflets — plan view — upper surface.

Element 15—illustrates a specimen of a leaf with 7 leaflets — plan view — upper surface.

Element 16—illustrates a specimen of a leaf with 3 leaflets — plan view — under surface.

Element 17—illustrates a specimen of a leaf with 5 leaflets — plan view — under surface.

Element 18—illustrates a specimen of a leaf with 7 leaflets — plan view — under surface.

DETAILED BOTANICAL DESCRIPTION

The chart used in the identification of the colors is that of The Royal Horticultural Society (The R.H.S. Colour Chart, 2001 edition), London, England. The terminology which precedes reference to the chart has been added to indicate the corresponding color in more common terms. The description is based on the observation of one-year-old specimens of the new variety during September while budded on their own roots and growing outdoors at Le Cannet des Maures, Var, France.

Botantical classification: *Rosa hybrida* cultivar MEICOSME.

Commercial classification: Bedding Rose Plant.

Plant:

*Habit*.—Bushy.

*Height*.—Approximately 100 cm on average.

*Width*.—Approximately 100 cm on average.

Branches:

*Color*.—Young stems: commonly near Yellow-Green Group 146D more or less suffused with near Greyed-Red Group 178B. Adult wood: commonly near Yellow-Green Group 146C.

*Length*.—From the crown to the flower is typically between 30 cm to 80 cm.

*Diameter*.—Typically between 0.4 cm to 1.0 cm on average.

*Young shoots*.—Anthocyanin coloration: absent.

*Thorns*.—Configuration on adult stems: rather elongated and curved downward on the upper surface and concave on the under surface. Long prickles — quantity: commonly 5 thorns per 10 cm long young stem and commonly 5 thorns per 10 cm long adult stem. Long prickles — length: typically between 0.6 cm to 0.8 cm on young stems and approximately 0.8 cm on average on adult stems. Long prickles — width: approximately 0.2 cm on average on young stems and approximately 0.3 cm on average on adult stems. Long prickles — base: shape is obovate; length is approximately 0.5 cm on average on young stems and approximately 0.7 cm on average on adult stems. Long prickles — color on young stems: commonly near Greyed-Purple Group 187D. Long prickles — color on adult stems: commonly near a Greyed-Orange Group 164B suffused with near Greyed-Orange Group 164A. Small prickles — quantity: absent.

*Internode*.—Numbers on the entire branch: typically between 10 to 24. Length: typically between 3.0 cm and 5.0 cm.

Foliage:

*General appearance*.—Dense, with a semi-glossy aspect.

*Number of leaflets*.—3, 5, 7; most often 7.

7 *leaflets leaf*.—Length: typically between 11.0 cm to 13.0 cm. Width: typically between 7.0 cm to 8.0 cm.

*Terminal leaflet*.—Length: typically between 4.5 cm to 5.5 cm. Width: typically between 3.0 cm to 3.5 cm.

*New foliage*.—Upper surface color: commonly near Green Group 137D more or less suffused with near Greyed-Purple Group 187B. Under surface color: commonly near Green Group 137D more or less suffused with near Greyed-Purple Group 187B.

*Adult foliage*.—Upper surface color: commonly near Green Group 137A. Under surface color: commonly near Green Group 138B. Anthocyanin coloration: absent.

Leaflets:

*Shape*.—Top: acuminate. Base: rounded.

*Glossiness of upper surface*.—Semi-glossy.

*Texture*.—Upper and under surfaces are leathery.

*General appearance*.—Oval.

*Serration*.—Small and single.

*Undulation on the margin*.—Weak.

*Venation*.—Color is commonly near Green Group 138B and pattern is imparipinnate.

*Petiole rachis*.—Color of upper surface: commonly near Green Group 137C. Color of under surface: commonly near Green Group 138B. Texture: upper surface is little glandular, under surface is very few prickles. Rachis of terminal leaflet: length is typically 5.0 cm to 6.5 cm and diameter is approximately 0.1 cm on average.

*Petioles*.—Upper surface: little glandular. Under surface: very few prickles. Color of upper surface: commonly near Green Group 137C. Color of under surface: commonly near Green Group 138B. Length: typically between 2.0 cm to 3.0 cm. Diameter: typically between 0.1 cm to 0.2 cm.

*Stipules*.—Length: typically between 1.3 cm to 1.5 cm. Width: typically between 0.2 cm to 0.3 cm. Color of upper surface: commonly near Green Group 137B. Color of under surface: commonly near Green Group 138A.

Inflorescence:

*Number of flowers per stem*.—Between 4 and 40 flowers per stem.

*Lastingness of the bloom*.—On the plant: approximately 3 weeks. In vase: not tested.

*Bud*.—Shape: conical. Size: small. Length: approximately 1.8 cm on average. Width: approximately 1.0 cm on average. Color as calyx breaks: upper surface: commonly near Red-Purple Group 67A suffused with near Red-Purple Group 63A, basal spot is very little and near Greyed-Yellow Group 162B. under surface: commonly near Red-Purple Group 61B, basal spot is very little and near Greyed-Yellow Group 162C.

*Sepals*.—Number: commonly 5. Length: typically between 1.5 cm to 1.8 cm. Width: typically between 0.6 cm to 0.7 cm. Shape: at the top: elongated and narrow. at the base: upright. Extensions: absent or very weak elongated extensions on 2 or 3 sepals, which number is between 1 and 3 per sepal; length is typically between 0.2 cm to 0.3 cm, and width is approximately 0.5 cm on average. Upper surface: texture: tomentous. color: commonly near Green Group 138C. Under surface: texture: smooth. color: commonly near Green Group 138A.

*Receptacle*.—Color: commonly near Green Group 138B. Length: approximately 0.6 cm on average. Width: approximately 0.5 cm on average. Surface: smooth. Shape: pitcher shaped.

*Peduncle*.—Length: typically between 1.2 cm to 1.7 cm. Width: approximately 0.15 cm on average. Surface: very slightly glandular. Color: commonly near Green Group 138B more or less suffused with near Greyed-Purple Group 185A.

*Flower*.—Average size when open: typically between 5.0 cm to 6.0 cm. Shape: flat cup shaped. Shape when viewed from above: irregular rounded. Shape of the upper part of the flower profile: flat. Shape of the lower part of the flower profile: flattened convex. Type: single. Number of petals under normal conditions: typically 5 petals. Petals: shape: dissymmetric rounded at the base and flat sometime lightly cordiform to the top. texture: more or less leathery. length: approximately 2.8 cm on average. width: approximately 3.0 cm on average. Undulation of the petal: very strong. Reflexing of the petal: absent. Petal incision: absent or very few. Petal arrangement: imbricated without petaloids. Petal drop: petals drop off cleanly before drying. Fragrance: none. Discoloration of the flower: the flowers remain on the plant for a long period and after the total end of the flowering; from the open flower stage to the petal drop stage, the color of the upper surface of the flower evolves from Red-Purple Group 67B to Red-Purple Group 65C. Color when opening: basal spot on the upper surface: commonly near Yellow-White Group 158B. upper surface: commonly near Red-Purple Group 67B. basal spot on the under surface: commonly near Yellow-White Group 158C. under surface: commonly near Red-Purple Group 74D. Color of the open flower: basal spot on the upper surface: commonly near Yellow-White Group 158B. upper surface of the flower: commonly near Red-Purple Group 67B. basal spot on the under surface: commonly near Yellow-White Group 158C. under surface of the flower: commonly near Red-Purple Group 74D. Anthers: number is 110 on average, length is approximately 0.1 cm on average, width is approximately 0.1 cm on average, coloration is commonly near Orange Group 24B, and arrangement is regular around styles. Filaments: length is typically between 0.3 cm and 0.9 cm and coloration is commonly near Greyed-Orange Group 163B. Styles: length is approximately 0.8 cm on average, coloration is commonly Greyed-Purple Group 185B, and number is typically between 20 to 25. Stigmas: length is less than 0.1 cm and coloration is commonly near Greyed-Yellow Group 160A. Pollen: color is commonly near Yellow-Orange Group 17A. Hips: shape is pear shaped; diameter is commonly 1.5 cm to 2.0 cm; length is approximately 1.5 cm on average; color is commonly near Orange Group 28A more or less covered with near Red Group 46A.

Seeds: width is commonly 0.3 cm to 0.5 cm; length is commonly 0.3 cm to 0.5 cm; color is commonly near Greyed-Yellow Group 162D.

Development:

*Vegetation*.—Very strong.

*Blooming*.—Early in the season, very abundant and nearly continuous typically from May to the first frosts in France.

*USDA hardiness zone*.—Zone 5 to 9.

*Tolerance to disease*.—Very good, and particularly against Black Spot (*Diplocarpon rosae*).

The new 'MEICOSME' variety has not been observed under all possible environmental conditions to date. Accordingly, it is possible that the phenotypic expression may vary somewhat with changes in light intensity and duration, cultural practices, and other environmental conditions.

I claim:

1. A new and distinct variety of rose plant named 'MEICOSME' characterized by the following combination of characteristics:

(a) forms dark pink purple colored flowers, (b) produces single flowers, and (c) exhibits a bushy growth habit;

substantially as herein shown and described.

* * * * *

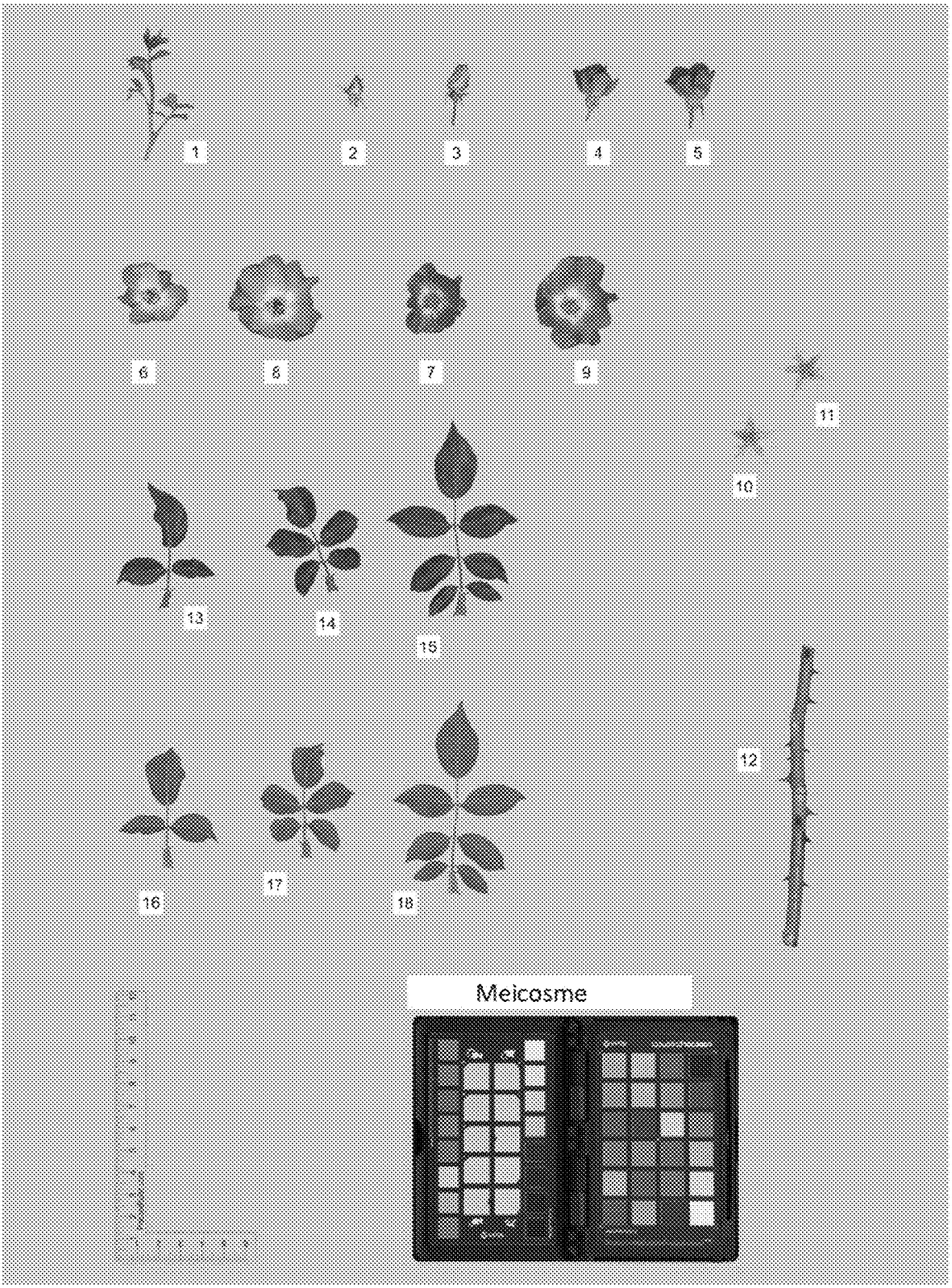
1
2
3
4
5
6
8
7
9
11
10
13
14
15
12
16
17
18
Meicosme